(12) United States Patent
Patel et al.

(10) Patent No.: US 11,670,013 B2
(45) Date of Patent: Jun. 6, 2023

(54) METHODS, SYSTEMS, AND COMPUTING PLATFORMS FOR PHOTOGRAPH OVERLAYING UTILIZING ANATOMIC BODY MAPPING

(71) Applicants: Jigar Patel, Woodbridge, VA (US); Ayushi Patidar, Woodbridge, VA (US); Parth Patidar, Woodbridge, VA (US)

(72) Inventors: Jigar Patel, Woodbridge, VA (US); Ayushi Patidar, Woodbridge, VA (US); Parth Patidar, Woodbridge, VA (US)

( * ) Notice: Subject to any disclaimer, the term of this patent is extended or adjusted under 35 U.S.C. 154(b) by 0 days.

(21) Appl. No.: 17/359,524

(22) Filed: Jun. 26, 2021

(65) Prior Publication Data

US 2021/0407152 A1    Dec. 30, 2021

Related U.S. Application Data

(60) Provisional application No. 63/044,532, filed on Jun. 26, 2020.

(51) Int. Cl.
| | |
|---|---|
| *G06T 11/00* | (2006.01) |
| *G16H 30/20* | (2018.01) |
| *A61B 5/00* | (2006.01) |
| *G06V 40/10* | (2022.01) |
| *G06V 40/16* | (2022.01) |

(52) U.S. Cl.
CPC ............. *G06T 11/00* (2013.01); *A61B 5/444* (2013.01); *A61B 5/4887* (2013.01); *G06V 40/10* (2022.01); *G06V 40/161* (2022.01); *G16H 30/20* (2018.01); *A61B 2576/02* (2013.01); *G06T 2210/41* (2013.01); *G06T 2210/62* (2013.01); *G06V 2201/03* (2022.01)

(58) Field of Classification Search
CPC . G06T 11/00; G06T 2210/41; G06T 2210/62; G16H 30/20; G06V 40/10; G06V 40/161; G06V 2201/03; A61B 5/444; A61B 5/4887; A61B 2576/02
USPC .......................................................... 345/592
See application file for complete search history.

(56) References Cited

U.S. PATENT DOCUMENTS

| | | | |
|---|---|---|---|
| 2004/0135788 A1* | 7/2004 | Davidson ................ G06T 15/00 345/530 |
| 2007/0248261 A1* | 10/2007 | Zhou ..................... G06T 19/006 382/154 |
| 2009/0066700 A1 | 3/2009 | Harding et al. |
| 2011/0158491 A1* | 6/2011 | Markova ............... G06T 3/0081 382/128 |
| 2012/0289826 A1 | 11/2012 | Graumann et al. |
| 2015/0100290 A1* | 4/2015 | Falt ........................ G16H 50/50 703/2 |

(Continued)

*Primary Examiner* — Jin Ge
(74) *Attorney, Agent, or Firm* — Howard University School of Law

(57) ABSTRACT

Methods, systems, and computing platforms are disclosed. Exemplary implementations may: identify and store anatomical landmarks on a first reference digital image of a region of a human body; insert biopsy site identification data on the first reference digital image with the anatomical landmarks to form a second reference digital image; transform the second reference digital image into a mesh mask image; and overlay the mesh mask image on a third digital image of the region of the human body.

12 Claims, 9 Drawing Sheets

(56) References Cited

U.S. PATENT DOCUMENTS

| | | | |
|---|---|---|---|
| 2015/0238271 A1 | 8/2015 | Wollowick et al. | |
| 2016/0071264 A1* | 3/2016 | Agam et al. | |
| 2017/0178540 A1* | 6/2017 | Rios | G09B 23/285 |
| 2018/0190035 A1* | 7/2018 | Grundhöfer | G06T 19/006 |
| 2018/0325605 A1 | 11/2018 | Scherr et al. | |
| 2019/0130792 A1 | 5/2019 | Rios et al. | |
| 2020/0375546 A1* | 12/2020 | Shoudy | A61B 5/7425 |

* cited by examiner

METHODS, SYSTEMS, AND COMPUTING PLATFORMS FOR PHOTOGRAPH OVERLAYING UTILIZING ANATOMIC BODY MAPPING

CROSS-REFERENCE TO RELATED APPLICATIONS

This application claims priority to provisional application App. No. 63/044,532 filed Jun. 26, 2020 the contents are incorporated by references herein.

FIELD

The present disclosure relates to methods, systems, and computing platforms for photograph overlaying utilizing anatomic mapping.

BACKGROUND

Skin cancers are the most common malignancy and the incidence of both nonmelanoma and melanoma cancers are increasing in the US. Wrong-site surgery for skin cancers is a preventable event, yet it is the most frequent serious error reported and the most common reason for malpractice claims amongst dermatologic surgeons. Ambiguity in identifying the correct site can result in treatment delay with increased morbidity due to progressive subclinical tumor growth necessitating a larger defect and potential for metastasis. The current standard workflow first involves a biopsy followed by definitive surgery. Due to multiple concurrent biopsy sites, treatment of background precancerous areas with liquid nitrogen cryotherapy, rapid skin healing and a delay of many weeks to surgery, localization of the tumor site after a biopsy is difficult. Accuracy in this setting is imperative as removing even 1 or 2 mm of healthy skin on areas such as the eye or nose can have deleterious effects on functional and aesthetic surgical outcomes.

Wrong-site surgery for skin cancer commonly occurs because of the lack of standardization of biopsy site photography across practices and providers, deterioration of image resolution when photos are transmitted to the surgeon, and challenges in accurately identifying the treatment site that can camouflage with nearby benign, cancerous, or precancerous lesions or prior scars.

There are limitations in how data is transferred across the various electronic health records (EHRs) used by dermatology practices in the US. Furthermore, the incidence of skin cancers is increasing rapidly as the current demographics shift to a more elderly population. As more and more surgeries are performed to treat these cancers going forward, patient safety will remain paramount to ensure precise identification of the correct site(s).

If a biopsy reveals a skin cancer, the patient is scheduled for surgery with the same clinician who did the biopsy or, more often, referred to a specialized skin cancer surgeon (Mohs micrographic surgeon). The biopsy photos are then faxed, e-mailed, or attached to the referral order (if the providers have access to the same EHR network). At the time of surgery, the office staff prints hard copies or pulls up the static photo on a for the surgeon to reference when locating the site to be treated. Unfortunately, given the lack of a standardized platform to easily take and view these images electronically, photo quality (especially with images transmitted via fax and/or printed) is often pixelated with poor resolution making it difficult to pinpoint the correct site.

The surgeon also relies on the location of the biopsy scar and patient report. However, given that several weeks or months often pass between biopsy and surgery, the skin heals quickly enabling the biopsy scar to blend in with the surrounding skin (especially on chronically sun-damaged areas such as the head and neck). Additionally, because this workflow usually involves two different providers (clinician who performs the biopsy and surgeon who treats the cancer), it increases the risk of human error and further compounds the risk of inaccurate identification of the surgical site.

There are several challenges associated with biopsy photography. First, the quality of images is often underappreciated. Most practices have nurses or medical assistants take these photos. Unfortunately, they are often not trained in which anatomic landmarks are most useful to include in images. Photographs are also taken too wide or too close, out of focus, or do not clearly identify the site and these shortcomings are realized too late at the time of surgery.

The rate of physician misidentification of the biopsy site is higher for patients who present with multiple locations that have been biopsied at the same time. Furthermore, a delay of greater than six weeks between biopsy and surgery is associated with an increased risk of site misidentification by clinicians. The interval from biopsy to surgery does not reflect the prolonged wait times seen in actual clinical practice. And patients presenting with multiple biopsy sites and background sun damage, a delay of weeks to months from biopsy to surgery, and/or site(s) located in an area not visible without a mirror can be an increased risk of site misidentification by clinicians.

Various methods to pinpoint sites based on anatomy have been proposed, including the triangulation method, which uses nearby landmarks to triangulate the location of the target lesion. However, such measurements are time-consuming and most clinicians forego these methods in practice. There is a need for an innovative solution to help alleviate this pain point and mitigate the risk of biopsy site misidentification.

SUMMARY

In light of the foregoing background, the following presents a simplified summary of the present disclosure in order to provide a basic understanding of some aspects of the disclosure. This summary is not an extensive overview of the disclosure. It is not intended to identify key or critical elements of the disclosure or to delineate the scope of the disclosure. The following summary merely presents some concepts of the disclosure in a simplified form as a prelude to the more detailed description provided below.

In some implementations of a method, a processor with machine-readable instructions utilizes camera images to confirm the location of cancerous skins cells for surgical removal on a human body. The machine-readable instructions identifies anatomical landmarks on a photo to pinpoint the location of cancerous cells at the time of biopsy. At the time of surgery, the machine-readable instructions implement its overlay feature to match the biopsy photo over top of the real-time human body image. Once the anatomical landmarks from the biopsy photo are matched with those of the human body patient, the surgeon is able to identify the site of skin for removal.

One aspect of the present disclosure relates to a computer implemented method which may include identifying and storing anatomical landmarks on a first reference digital image of a region of a human body. The method may include inserting or receiving biopsy site identification data on the first reference digital image with the anatomical landmarks to form a second reference digital image. The method may include transforming the second reference digital image into a mesh mask image. The method may include overlaying the mesh mask image on a third digital image of the region of the human body.

One aspect of the present disclosure relates to a computer implemented method which may include identifying and storing anatomical landmarks on a first reference digital image of a region of a human body. The method may include inserting or receiving biopsy site identification data on the first reference digital image with the anatomical landmarks to form a second reference digital image. The method may include transforming the second reference digital image into an adjustable transparent mask image. The method may include overlaying the adjustable transparent mask image on a third digital image of the region of the human body.

In some implementations of the method, it may include further including storing the first reference digital image in a non-transitory computer readable storage.

In some implementations of the method, the third digital image including a real-time format.

In some implementations, a computer-implemented method that uses a photograph overlay to superimpose anatomical landmarks for a patient photograph at the time of biopsy on anatomical landmarks on a current photograph of that patient in order to identify the point of biopsy in anticipation of surgery and other procedures.

In one aspect, a computer implemented method captures and stores photographs and identifies anatomical landmarks on an initial reference image taken through a phone software application in order to facilitate biopsy site identification. The method utilizes a combination of cloud computing model to facilitate anatomic detection and mapping.

In one aspect, a computer implemented method which transforms an initial reference image with a marked biopsy site into a transparent or mesh mask image that can be matched to a second image taken at time of surgery.

In one aspect, a method of anatomic mapping which uses user data to improve body region mapping through enhancing the preciseness of anatomical landmark identification with the inputting of more images by users.

In one aspect, the computerized feature recognition enhances accuracy in an efficient and user-friendly workflow. This feature coupled with tools such as adjustable transparency and pinch-to-zoom will facilitate correct site identification for all patients, decrease medico-legal risk, and increase both patient and physician confidence prior to surgery.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of 'a', 'an', and 'the' include plural referents unless the context clearly dictates otherwise.

DETAILED DESCRIPTION

Referring to FIGS. 1-8B, methods, systems, and computing platforms generally utilizes digital images to confirm the location of cancerous skins cells for surgical removal. Various implementations of methods, systems, and computing platforms with machine readable instructions may identify anatomical landmarks on digital photo to pinpoint the location of cancerous cells at the time of biopsy. At the time of surgery, an application may use an overlay feature to match the biopsy photo over top of the real-time live patient's image. Once the anatomical landmarks from the biopsy photo are matched with those of the live patient, the surgeon is able to identify the site of skin for removal.

Figure 1:
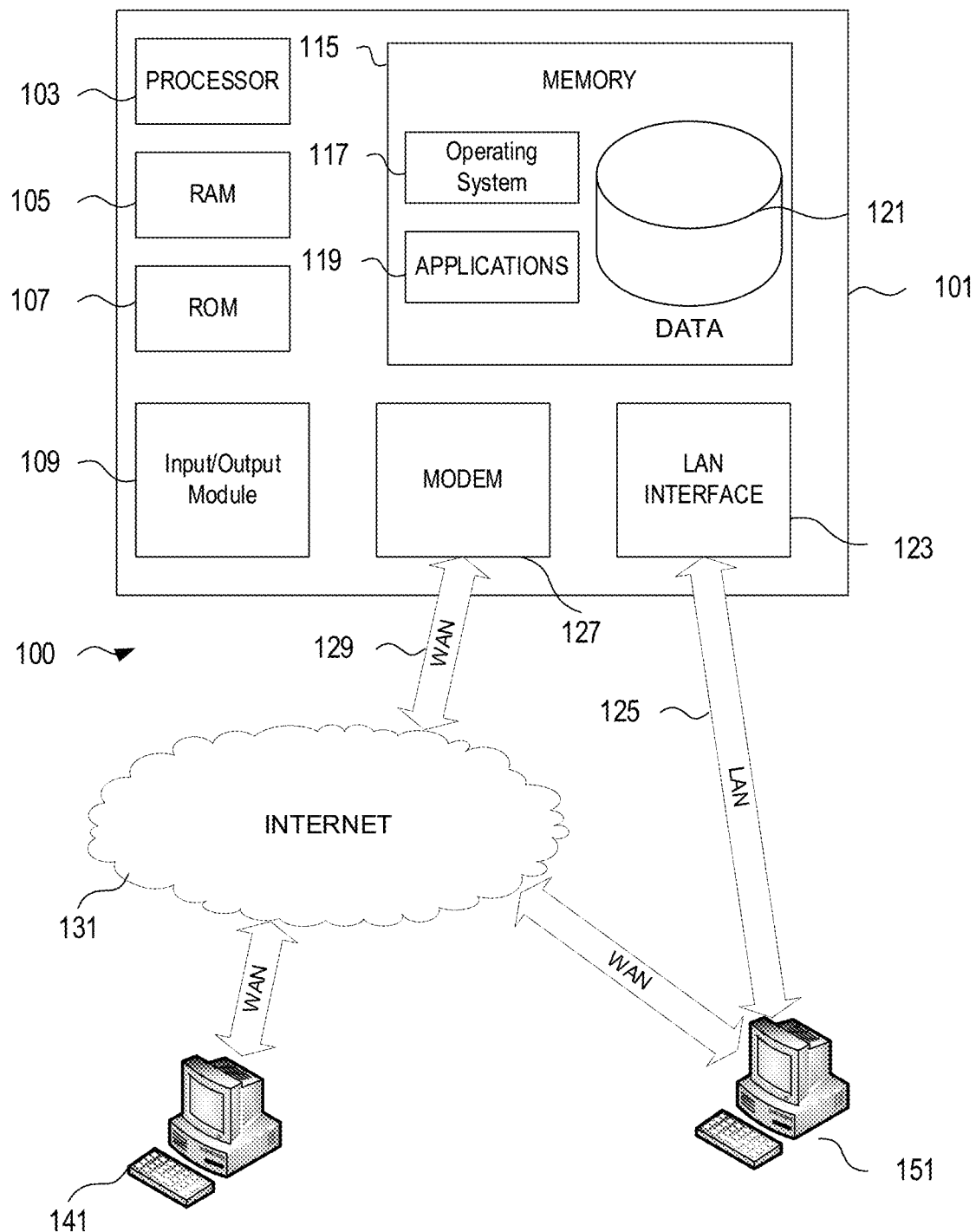
FIG. 1 illustrates a schematic diagram of a digital computing environment in which certain aspects of the present disclosure may be implemented.

FIG. 1 illustrates a block diagram of a specific programmed computing device 101 (e.g., a computer server) that may be used according to an illustrative embodiment of the disclosure. The computer server 101 may have a processor 103 for controlling overall operation of the server and its associated components, including RAM 105, ROM 107, input/output module 109, and memory 115.

Input/Output (I/O) 109 may include a microphone, keypad, touch screen, camera, and/or stylus through which a user of device 101 may provide input, and may also include one or more of a speaker for providing audio output and a video display device for providing textual, audiovisual and/or graphical output. Other I/O devices through which a user and/or other device may provide input to device 101 also may be included. Software may be stored within memory 115 and/or storage to provide computer readable instructions to processor 103 for enabling server 101 to perform various technologic functions. For example, memory 115 may store software used by the server 101, such as an operating system 117, application programs 119, and an associated database 121. Alternatively, some or all of server 101 computer executable instructions may be embodied in hardware or firmware (not shown). As described in detail below, the database 121 may provide centralized storage of characteristics associated with vendors and patrons, allowing functional interoperability between different elements located at multiple physical locations.

The server 101 may operate in a networked environment supporting connections to one or more remote computers, such as terminals 141 and 151. The terminals 141 and 151 may be personal computers or servers that include many or all of the elements described above relative to the server 101. The network connections depicted in FIG. 1 include a local area network (LAN) 125 and a wide area network (WAN) 129, but may also include other networks. When used in a LAN networking environment, the computer 101 is connected to the LAN 125 through a network interface or adapter 123. When used in a WAN networking environment, the server 101 may include a modem 127 or other means for establishing communications over the WAN 129, such as the Internet 131. It will be appreciated that the network connections shown are illustrative and other means of establishing a communications link between the computers may be used. The existence of any of various well-known protocols such as TCP/IP, Ethernet, FTP, HTTP and the like is presumed.

Computing device 101 and/or terminals 141 or 151 may also be mobile terminals such as smart phone including various other components, such as a battery, speaker, and antennas (not shown).

The disclosure is operational with numerous other special purpose computing system environments or configurations. Examples of computing systems, environments, and/or configurations that may be suitable for use with the disclosure include, but are not limited to, personal computers, server computers, hand-held or laptop devices, multiprocessor systems, microprocessor-based systems, set top boxes, programmable consumer electronics, network PCs, minicomputers, mainframe computers, mobile computing devices, e.g., smart phones, wearable computing devices, tablets, distributed computing environments that include any of the above systems or devices, and the like.

The disclosure may be described in the context of computer-executable instructions, such as program modules, being executed by a computer. Generally, program modules include routines, programs, objects, components, data structures, etc. that perform particular tasks or implement particular computer data types. The disclosure may also be practiced in distributed computing environments where tasks are performed by remote processing devices that are linked through a communications network. In a distributed computing environment, program modules may be located in both local and remote computer storage media including memory storage devices.

Figure 2:
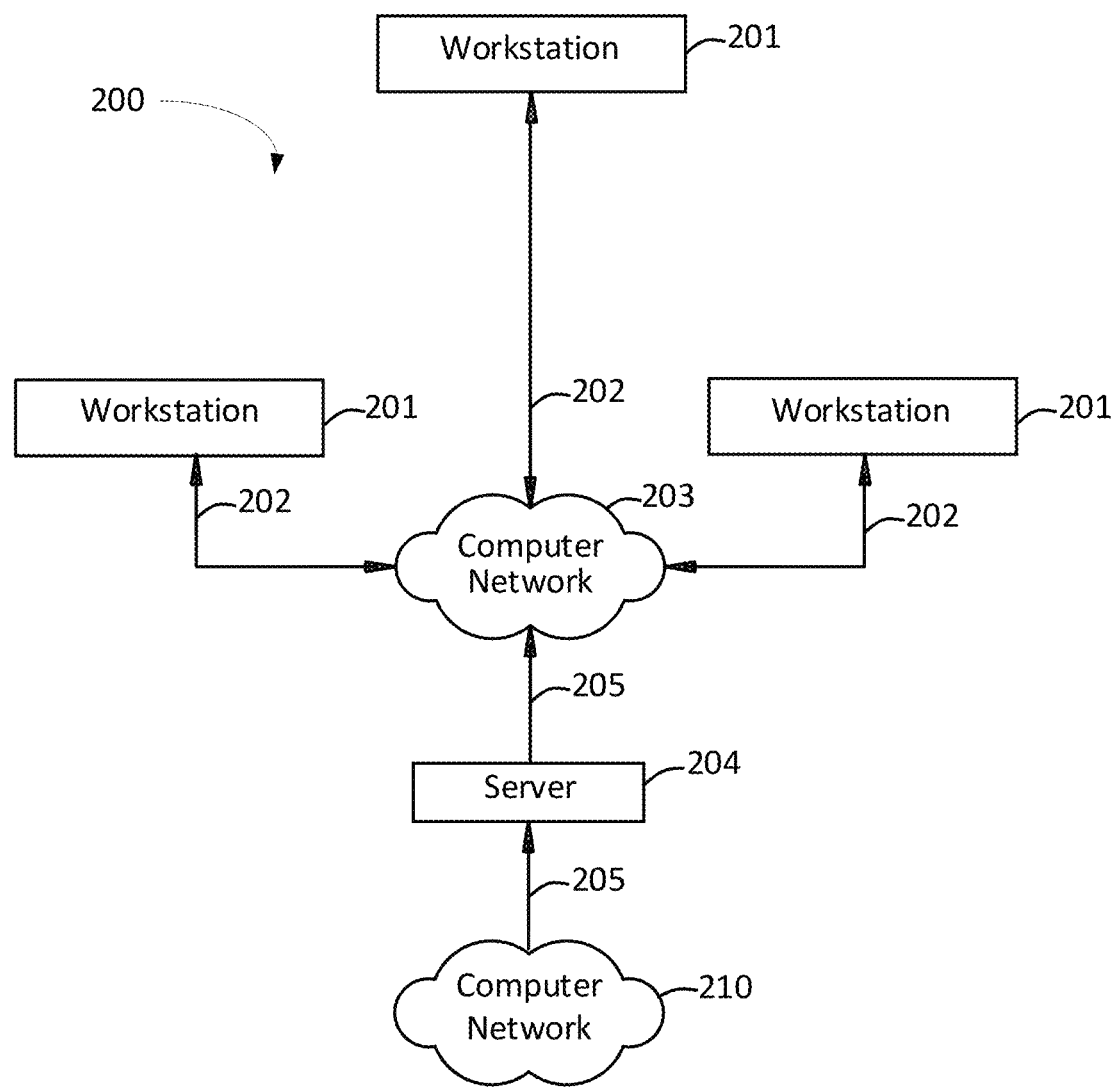
FIG. 2 is an illustrative block diagram of workstations and servers that may be used to implement the processes and functions of certain embodiments of the present disclosure.

Referring to FIG. 2, an illustrative system 200 for implementing methods according to the present disclosure is shown. As illustrated, system 200 may include one or more workstations 201. Workstations 201 may be local or remote, and are connected by one or more communications links 202 to computer networks 203, 210 that is linked via communications links 205 to server 204. In system 200, server 204 may be any suitable server, processor, computer, or data processing device, or combination of the same. Computer networks 203, 201 may incorporate various machine intelligence (MI) neutral network features of available Tensorflow or Neuroph software development platforms (which are incorporated by reference herein).

Computer network 203 may be any suitable computer network including the Internet, an intranet, a wide-area network (WAN), a local-area network (LAN), a wireless network, a digital subscriber line (DSL) network, a frame relay network, an asynchronous transfer mode (ATM) network, a virtual private network (VPN), or any combination of any of the same. Communications links 202 and 205 may be any communications links suitable for communicating between workstations 201 and server 204, such as network links, dial-up links, wireless links, hard-wired links, etc.

Figure 3:
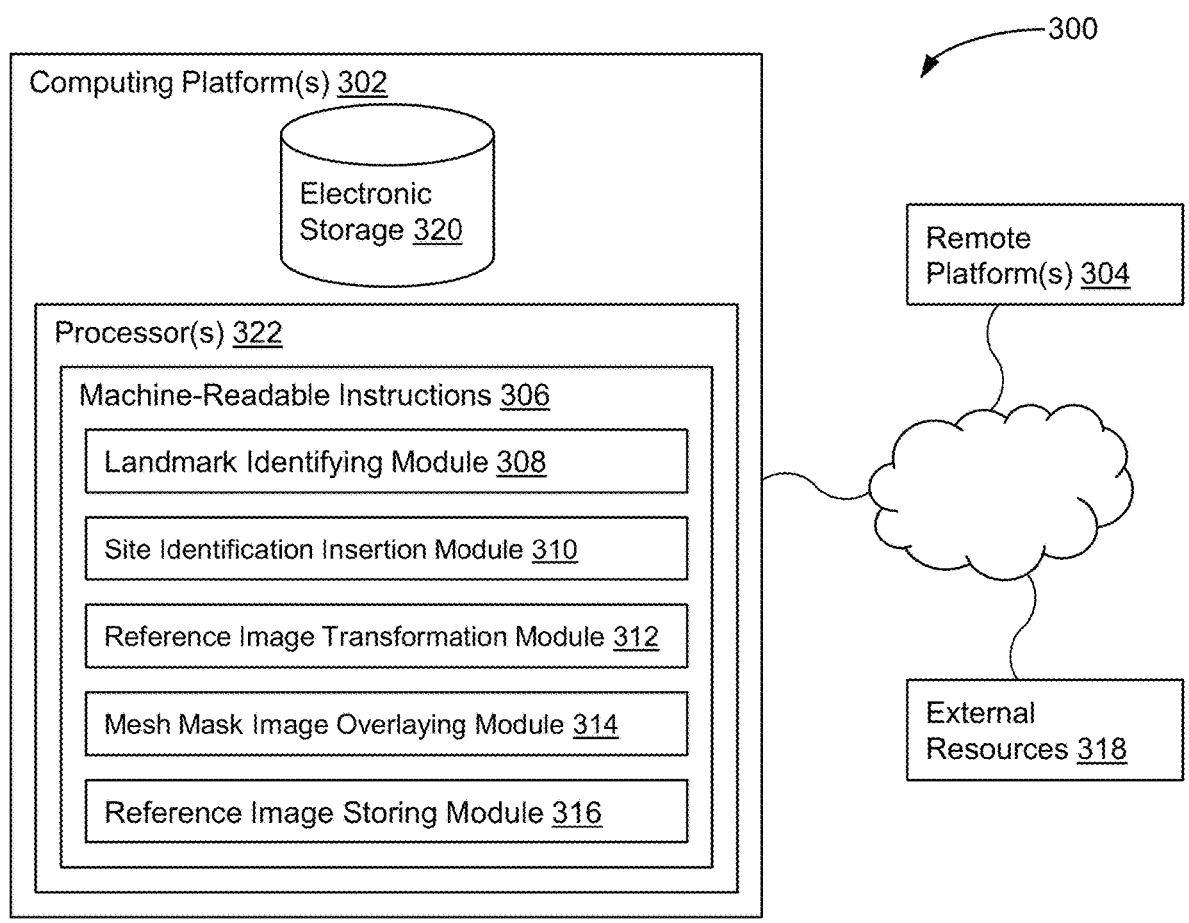
FIG. 3 illustrates a system configured for overlaying utilizing facial or any body region mapping, in accordance with one or more implementations.

FIG. 3 illustrates a system 300 configured in accordance with one or more implementations. The disclosure may be described in the context of cloud-based computing architecture employing Amazon Web Service (AWS). Nevertheless, other commercially available cloud-based services may be used, such as Microsoft Azure, and Google Cloud. The system 300 components may be provided in the AWS cloud and have been architected to scale in a resilient manner through the use of technologies chosen without any legacy dependencies. In some implementations, system 300 may include one or more computing platforms 302. Computing platform(s) 302 may be configured to communicate with one or more remote platforms 304 according to a client/server architecture, a peer-to-peer architecture, cloud-based architecture and/or other architectures. Remote platform(s) 304 may be configured to communicate with other remote platforms via computing platform(s) 302 and/or according to a client/server architecture, a peer-to-peer architecture, and/or other architectures. Users may access system 300 via remote platform(s) 304.

Computing platform(s) 302 may be configured by machine-readable instructions 306. Machine-readable instructions 306 may include one or more instruction modules. The instruction modules may include computer program modules. The instruction modules may include one or more of landmark identifying module 308, site identification insertion module 310, reference image transformation module 312, mesh mask image overlaying module 314, reference image storing module 316, and/or other instruction modules.

Landmark identifying module 308 may be configured with a system algorithm with multivariable equations including machine intelligence (MI) to identify and storing anatomical landmarks on a first reference digital image of a region of the human body. Module 308 may be activated on the clinic's secured smart device, such as mobile phone 151.

In one implementation, module 308 may incorporate an open source software development FaceDetector library (by Google Mobile Vision) which is incorporated by reference herein). Landmark identifying module 308 detects faces or body part in an image and upon detection it returns x and y coordinates of different anatomic landmark features on the face or body part. In one implementation, module 308 may continuously try to detect faces or body part from the camera image every second. Using an example implementation of a body part, such as a face. Once a face is detected, module 308 would return various attribute data below:

faceID (number)—a face identifier (used for tracking, if the same face appears on consecutive frames it will have the same faceID).

bounds (object)—an object containing:

origin ({x: number, y: number})—position of the top left corner of a square containing the face in view coordinates, size ({width: number, height: number})—size of the square containing the face in view coordinates, rollAngle (number)—roll angle of the face (bank), yawAngle (number)—yaw angle of the face (heading, turning head left or right), smilingProbability (number)—probability that the face is smiling, leftEarPosition ({x: number, y: number})—position of the left ear in view coordinates, rightEarPosition ({x: number, y: number})—position of the right ear in view coordinates, leftEyePosition ({x: number, y: number})—position of the left eye in view coordinates, leftEyeOpenProbability (number)—probability that the left eye is open, rightEyePosition ({x: number, y: number})—position of the right eye in view coordinates, rightEyeOpenProbability (number)—probability that the right eye is open, leftCheekPosition ({x: number, y: number})—position of the left cheek in view coordinates, rightCheekPosition ({x: number, y: number})—position of the right cheek in view coordinates, mouthPosition ({x: number, y: number})—position of the center of the mouth in view coordinates, leftMouthPosition ({x: number, y: number})—position of the left edge of the mouth in view coordinates, rightMouthPosition ({x: number, y: number})—position of the right edge of the mouth in view coordinates, and noseBasePosition ({x: number, y: number})—position of the nose base in view coordinates.

Module 308 saves the above values with the captured image in a database 121, storage 320 or cloud storage 340.

Figure 5A:
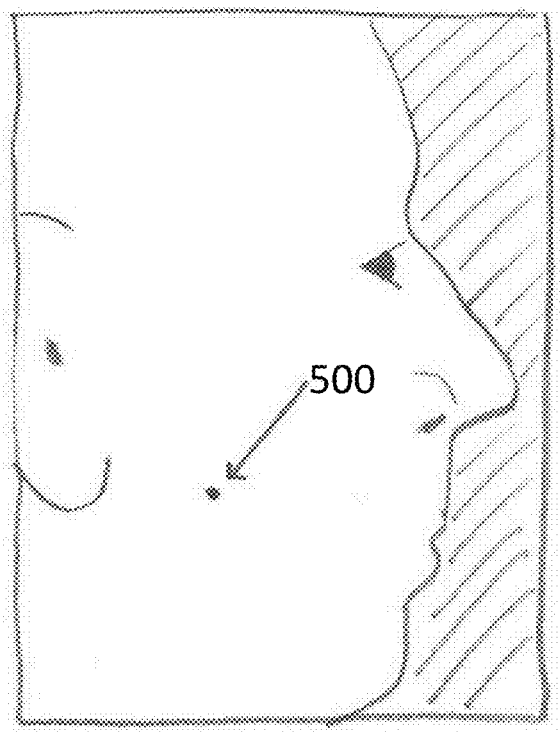
FIG. 5A illustrates a schematic diagram of an example patient presented with a concerning lesion on the right cheek of a facial region in accordance with one or more implementations.
Figure 5B:
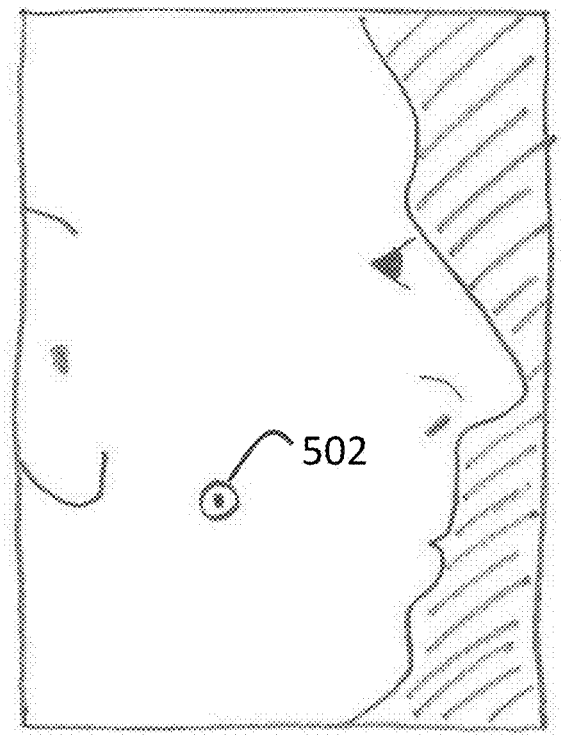
FIG. 5B illustrates a schematic diagram with a biopsy site circled on the example patient with a surgical digital marking pen and/or with a digital marker, digital photo taken via smart device camera with application, in accordance with one or more implementations.

Referring to FIGS. 3, 5A and 5B, site identification insertion module 310 may be configured with a system algorithm with multivariable equations including machine learning intelligence (MI) to insert biopsy site identification 502 on the first reference digital image over cancerous cells 500 with the anatomical landmarks to form a second reference digital image. In one in-use operation, the clinician photographs a biopsy site 502 using the smart device camera. If the surgical site is not denoted with a digital pen, the clinician can also optionally add a digital mark on the first reference digital image to denote the site and also add any additional notes.

Figures 6A, 6B:
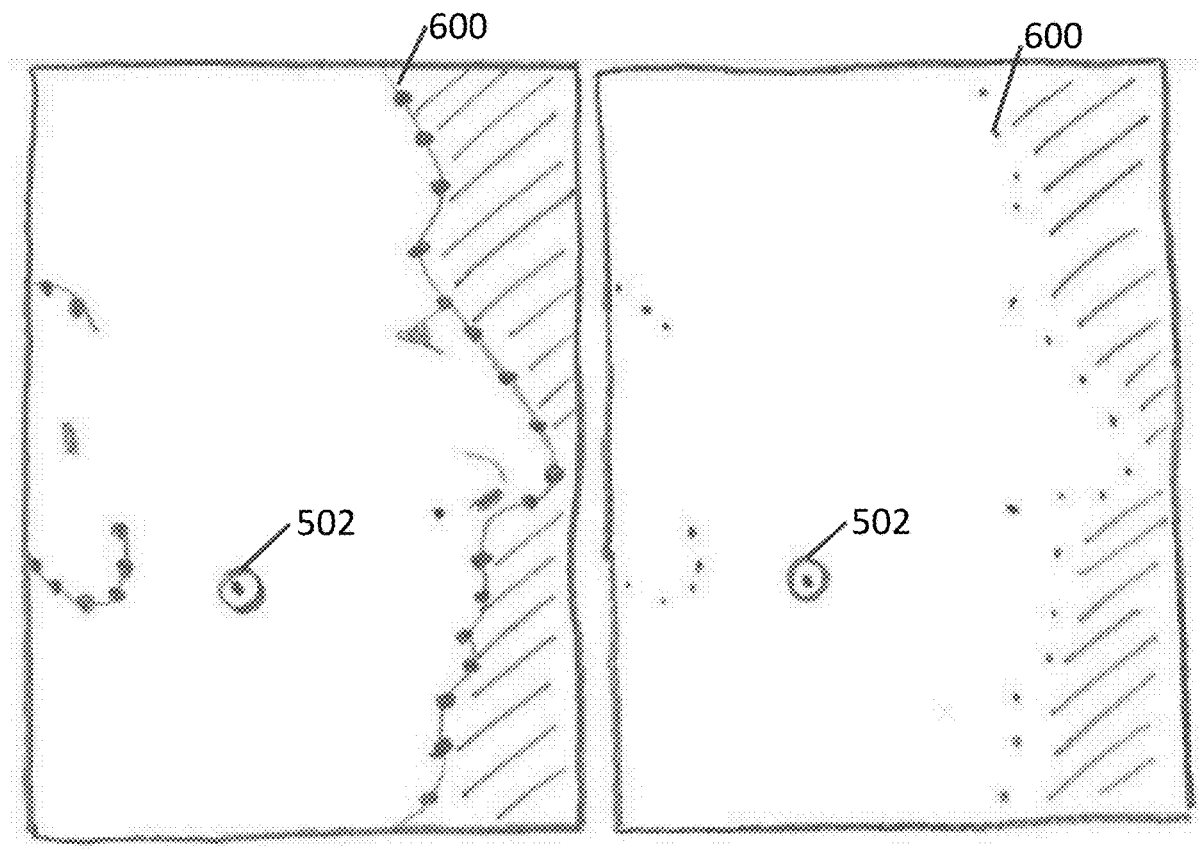
FIG. 6A illustrates a schematic diagram an image with relevant anatomic anchor points and/or landmarks, captured on a photo of facial region and translated raw image with mask/mesh image superimposed thereon in accordance with one or more implementations.
FIG. 6B illustrates a schematic diagram of a mask mesh image processed in FIG. 6A, in accordance with one or more implementations.
Figure 7A:
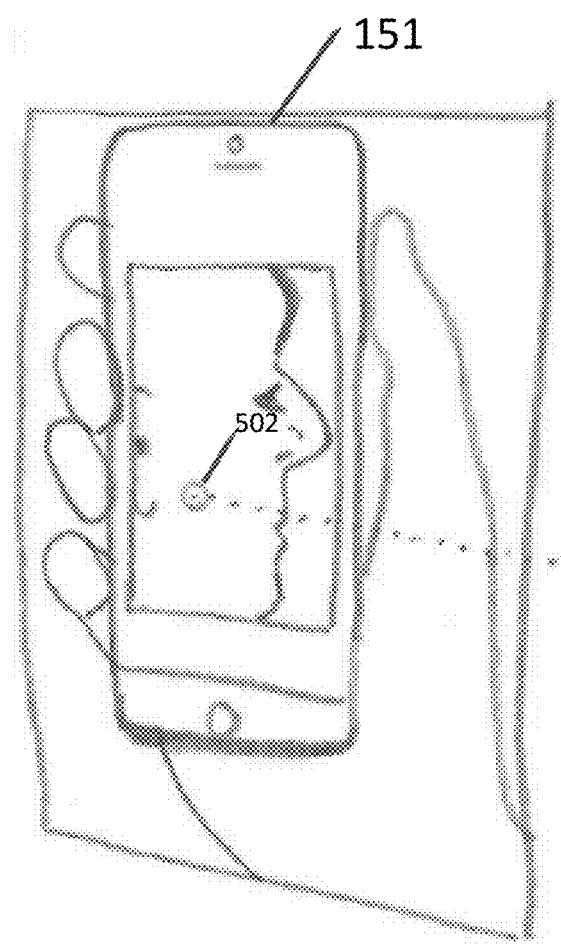
FIG. 7A illustrates a schematic diagram of a smart device with image displaying biopsy photo at a predefined transparency in which the smart device is positioned to align overlay to a real-time image of a patient facial region displayed on screen via a rear-view camera of the smart device, in accordance with one or more implementations.
Figure 7B:
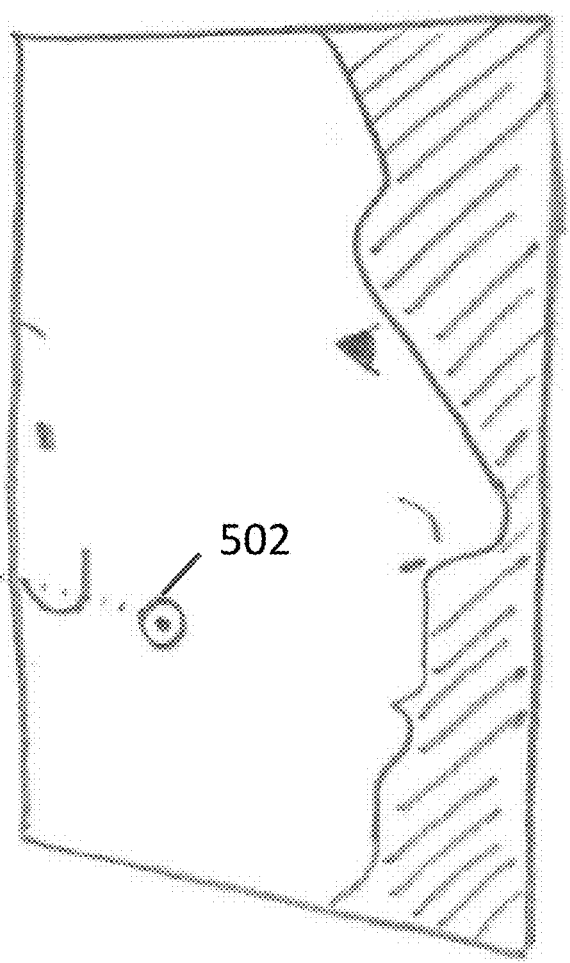
FIG. 7B illustrates an enlarged schematic diagram the real-time image in the smart device of FIG. 7A, in accordance with one or more implementations.
Figure 8A:
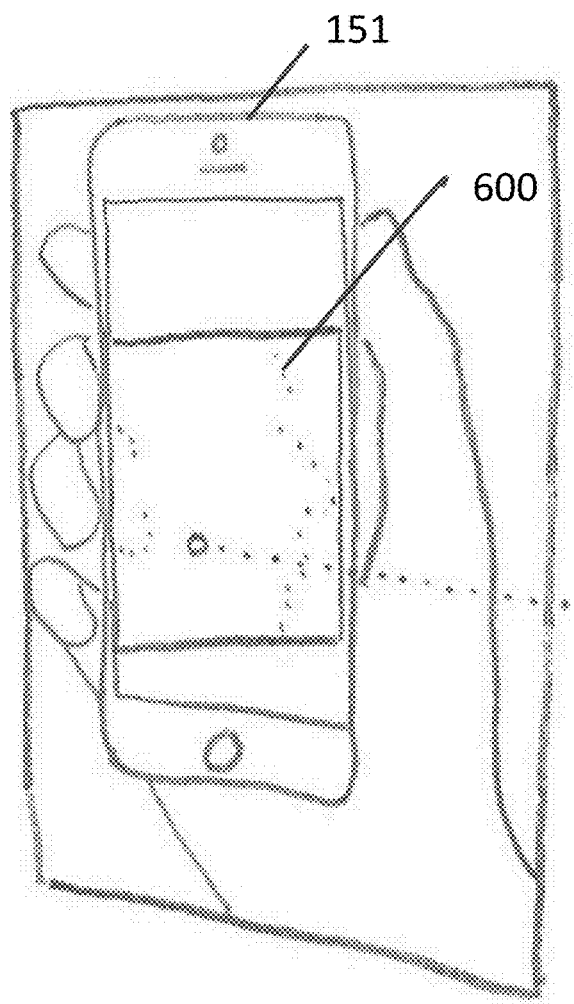
FIGS. 8A and 8B illustrates a schematic diagram of a smart device with displaying patient's anatomic mask/mesh image in which the smart device is positioned to align overlay of the anatomic anchor points to real-time image of live patient displayed on screen via rear-view camera generation with an anatomic outline mapped from relevant landmarks and anchor points, and site verification via adjustable overlay at the time of surgery, in accordance with one or more implementations.
Figure 8B:
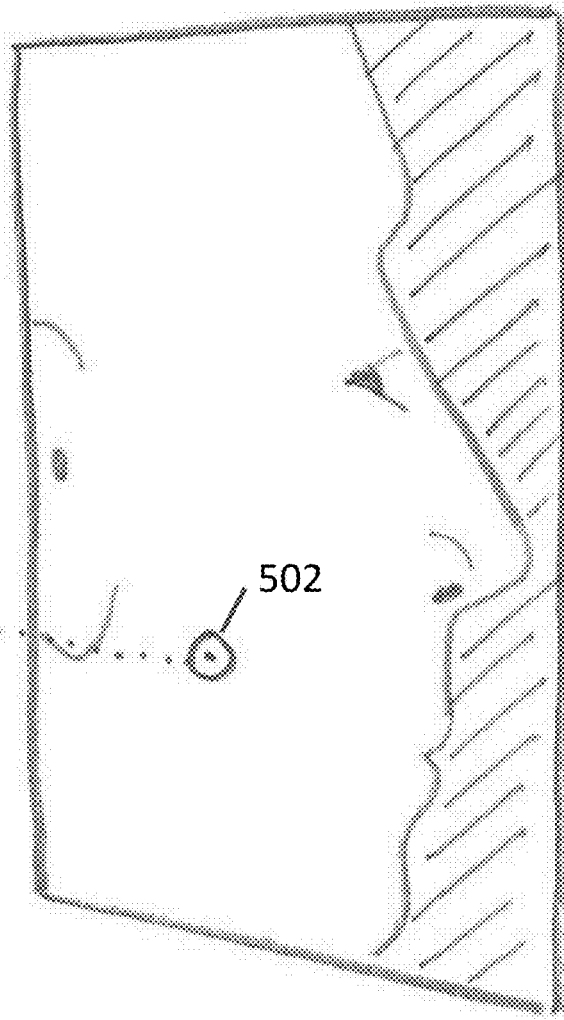

Referring to FIGS. 3, 6A and 6B, reference image transformation module 312 may be configured with a system algorithm with multivariable equations including machine intelligence (MI) to transform the second reference digital image into a mesh mask image 600.

In some other constructions, modules 312 and 314 implements deep learning machine learning techniques implementing representation of learning methods that allows a machine to be given raw data and determine the representations needed for data classification. Deep learning is a subset of machine learning that uses a set of algorithms to model high-level abstractions in data using a deep graph with multiple processing layers including linear and non-linear transformations. While many machine learning systems are seeded with initial features and/or network weights to be modified through learning and updating of the machine learning network, a deep learning network trains itself to identify "good" features for analysis. Using a multilayered architecture, machines employing deep learning techniques can process raw data better than machines using conventional machine learning techniques. Examining data for groups of highly correlated values or distinctive themes is facilitated using different layers of evaluation or abstraction.

Deep learning ascertains structure in data sets using backpropagation algorithms which are used to alter internal parameters (e.g., node weights) of the deep learning machine. Deep learning machines can utilize a variety of multilayer architectures and algorithms. While machine learning, for example, involves an identification of features to be used in training the network, deep learning processes raw data to identify features of interest without the external identification.

Mesh mask image overlaying module 314 may be configured with a system algorithm with multivariable equations to overlay the mesh mask image 600 on a third digital image of the region of the human body. The third digital image including a real-time format of a patient.

Overlaying module 314 processes these images to be overlaid onto the live image (e.g. third digital image) of the patient that is captured via the smart device 151 camera. Utilizing the system 300, the surgeon displays the biopsy site photo on the device screen using the various smart overlay option implementations. In one implementation, the original image (e.g. first reference digital image) at adjustable transparency and zoom (See FIGS. 7A and 7B). In another implementation, the transparency may be adjustable from 0 to 100%. In another implementation, the overlay image can also be magnified using a pinch-zoom feature.

In another implementation of module 314, an anatomic outline is generated from relevant landmarks, anchor points, and/or depth map (See FIGS. 6A, 6B, 8A and 8B). In one implementation, anatomic boundaries may be generated by machine learning (Ml) methods. In one implementation, anchor points can include any combination of anatomic structures or background lesions (e.g. moles, keratoses, sun spots, etc.).

In one implementation of module 314, depth points that measure the distance from the patient to the camera can also be extracted from the original image to help guide the surgeon to the appropriate distance to align images. In one implementation of module 314, anatomic silhouette (see FIG. 8A) can also be generated by subtracting the background of an image to highlight the natural curvature and lines of the relevant anatomic location (e.g. face, arm, back, etc.).

In one implementation of module 314, the device distance and angle from the patient can be adjusted so as to overlay the semi-transparent biopsy photo (e.g., an adjustable transparent mask image) or anatomic outline with the live image displayed by the rear camera view of the patient to verify that the circled biopsy sites are aligned. In one implementation of module 314, the computer readable instructions may automatically detect alignment and denote when the images are aligned precisely with either an audio, vibratory, color, or other cues.

In one implementation of module 314, methodology can also be applied to: precise alignment of overlaid magnified images of moles or other skin lesions to determine if any changes have occurred from the initial index image. Precise alignment of overlaid histological slides with various tissue stains to determining if/where staining corresponds to cells or region of interest.

Reference image storing module 316 may be configured to store the first, second, and third reference digital image in a computer storage. In one implementation, when the patient presents for surgery, the surgeon circles the presumed site based on the scar and available photo(s) within the EHR following the standard workflow. Then, the surgeon engages the system 300 on the clinic smart device 151 and selects the appropriate photo(s) based on the date and location of the biopsy. Alternatively, or in addition, there is also provided a feature to digitally import any digital image format taken by any digital camera or another smart device into the software application. System 300 application processes these images to be overlaid onto the live image of the patient that is captured via the smart device camera.

In some implementations, computing platform(s) 302, remote platform(s) 304, and/or external resources 318 may be operatively linked via one or more electronic communication links. For example, such electronic communication links may be established, at least in part, via a network such as the Internet and/or other networks. It will be appreciated that this is not intended to be limiting, and that the scope of this disclosure includes implementations in which computing platform(s) 302, remote platform(s) 304, and/or external resources 318 may be operatively linked via some other communication media.

A given remote platform 304 may include one or more processors configured to execute computer program modules. The computer program modules may be configured to enable an expert or user associated with the given remote platform 304 to interface with system 300 and/or external resources 318, and/or provide other functionality attributed herein to remote platform(s) 304. By way of non-limiting example, a given remote platform 304 and/or a given computing platform 302 may include one or more of a server, a desktop computer, a laptop computer, a handheld computer, a tablet computing platform, a NetBook, a Smartphone, and/or other computing platforms.

External resources 318 may include sources of information outside of system 300, external entities participating with system 300, and/or other resources. In some implementations, some or all of the functionality attributed herein to external resources 318 may be provided by resources included in system 300.

Computing platform(s) 302 may include electronic storage 320, one or more processors 322, and/or other components. Computing platform(s) 302 may include communication lines, or ports to enable the exchange of information with a network and/or other computing platforms. Illustration of computing platform(s) 302 in FIG. 3 is not intended to be limiting. Computing platform(s) 302 may include a plurality of hardware, software, and/or firmware components operating together to provide the functionality attributed herein to computing platform(s) 302. For example, computing platform(s) 302 may be implemented by a cloud of computing platforms operating together as computing platform(s) 302.

Electronic storage 320 may comprise non-transitory storage media that electronically stores information. The electronic storage media of electronic storage 320 may include one or both of system storage that is provided integrally (i.e., substantially non-removable) with computing platform(s) 302 and/or removable storage that is removably connectable to computing platform(s) 302 via, for example, a port (e.g., a USB port, a firewire port, etc.) or a drive (e.g., a disk drive, etc.). Electronic storage 320 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 320 may include one or more virtual storage resources (e.g., cloud storage, a virtual private network, and/or other virtual storage resources). Electronic storage 320 may store software algorithms, information determined by processor(s) 322, information received from computing platform(s) 302, information received from remote platform(s) 304, and/or other information that enables computing platform(s) 302 to function as described herein.

Processor(s) 322 may be configured to provide information processing capabilities in computing platform(s) 302. As such, processor(s) 322 may include one or more of a digital processor, an analog processor, a digital circuit designed to process information, an analog circuit designed to process information, a state machine, and/or other mechanisms for electronically processing information. Although processor(s) 322 is shown in FIG. 3 as a single entity, this is for illustrative purposes only. In some implementations, processor(s) 322 may include a plurality of processing units. These processing units may be physically located within the same device, or processor(s) 322 may represent processing functionality of a plurality of devices operating in coordination.

Processor(s) 322 may be configured to execute modules 308, 310, 312, 314, and/or 316, and/or other modules. Processor(s) 322 may be configured to execute modules 308, 310, 312, 314, and/or 316, and/or other modules by software; hardware; firmware; some combination of software, hardware, and/or firmware; and/or other mechanisms for configuring processing capabilities on processor(s) 322. As used herein, the term "module" may refer to any component or set of components that perform the functionality attributed to the module. This may include one or more physical processors during execution of processor readable instructions, the processor readable instructions, circuitry, hardware, storage media, or any other components.

It should be appreciated that although modules 308, 310, 312, 314, and/or 316 are illustrated in FIG. 3 as being implemented within a single processing unit, in implementations in which processor(s) 322 includes multiple processing units, one or more of modules 308, 310, 312, 314, and/or 316 may be implemented remotely from the other modules. The description of the functionality provided by the different modules 308, 310, 312, 314, and/or 316 described below is for illustrative purposes, and is not intended to be limiting, as any of modules 308, 310, 312, 314, and/or 316 may provide more or less functionality than is described. For example, one or more of modules 308, 310, 312, 314, and/or 316 may be eliminated, and some or all of its functionality may be provided by other ones of modules 308, 310, 312, 314, and/or 316. As another example, processor(s) 322 may be configured to execute one or more additional modules that may perform some or all of the functionality attributed below to one of modules 308, 310, 312, 314, and/or 316.

Figure 4A:
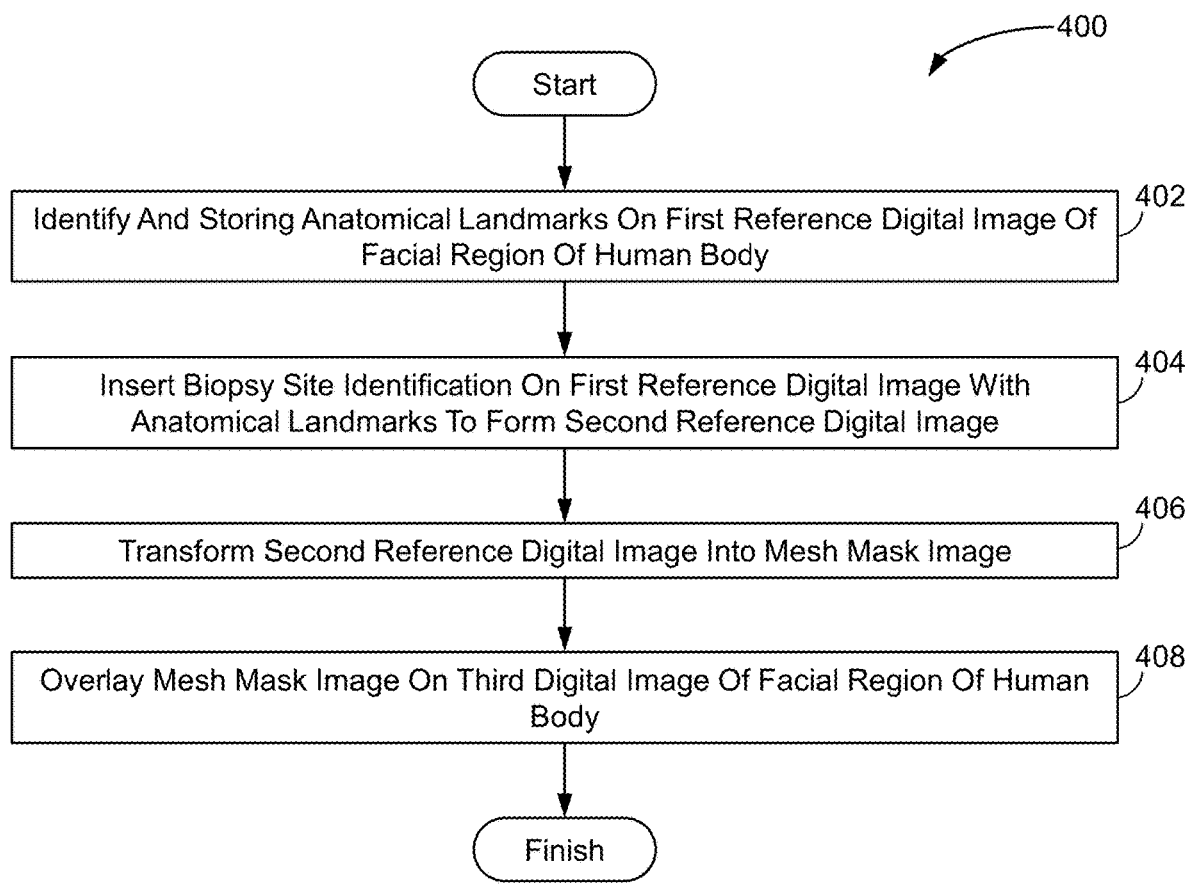
FIGS. 4A and/or 4B illustrates a method for overlaying utilizing facial or any body region mapping, in accordance with one or more implementations.

FIGS. 4A and/or 4B illustrates a method overlaying utilizing anatomic mapping, in accordance with one or more implementations. Electronic processing and documentation of biopsy sites utilizing smart devices can enable easily accessible, portable, and transferable images that can be referenced through an application to enhance accurate and precise identification of the surgical site. This digital technology of system 300 can transform current workflows in dermatology to ensure the highest patient safety standards in this field. The operations of method 400 presented below are intended to be illustrative. In some implementations, method 400 may be accomplished with one or more additional operations not described, and/or without one or more of the operations discussed. Additionally, the order in which the operations of method 400 are illustrated in FIGS. 4A and/or 4B and described below is not intended to be limiting.

In some implementations, method 400 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 400 in response to instructions stored electronically on an electronic storage medium. The one or more processing devices may include one or more devices configured through hardware, firmware, and/or software to be specifically designed for execution of one or more of the operations of method 400.

FIG. 4A illustrates method 400, in accordance with one or more implementations. An operation 402 may include identifying and storing anatomical landmarks on a first reference digital image of a region of a human body. Operation 402 may be performed by one or more hardware processors configured by machine-readable instructions including a module that is the same as or similar to landmark identifying module 308, in accordance with one or more implementations.

An operation 404 may include inserting biopsy site identification on the first reference digital image with the anatomical landmarks to form a second reference digital image. Operation 404 may be performed by one or more hardware processors configured by machine-readable instructions including a module that is the same as or similar to site identification insertion module 310, in accordance with one or more implementations.

An operation 406 may include transforming the second reference digital image into a mesh mask image. Operation 406 may be performed by one or more hardware processors configured by machine-readable instructions including a module that is the same as or similar to reference image transformation module 312, in accordance with one or more implementations.

An operation 408 may include overlaying the mesh mask image on a third digital image of the region of the human body. Operation 408 may be performed by one or more hardware processors configured by machine-readable instructions including a module that is the same as or similar to mesh mask image overlaying module 314, in accordance with one or more implementations.

Figure 4B:
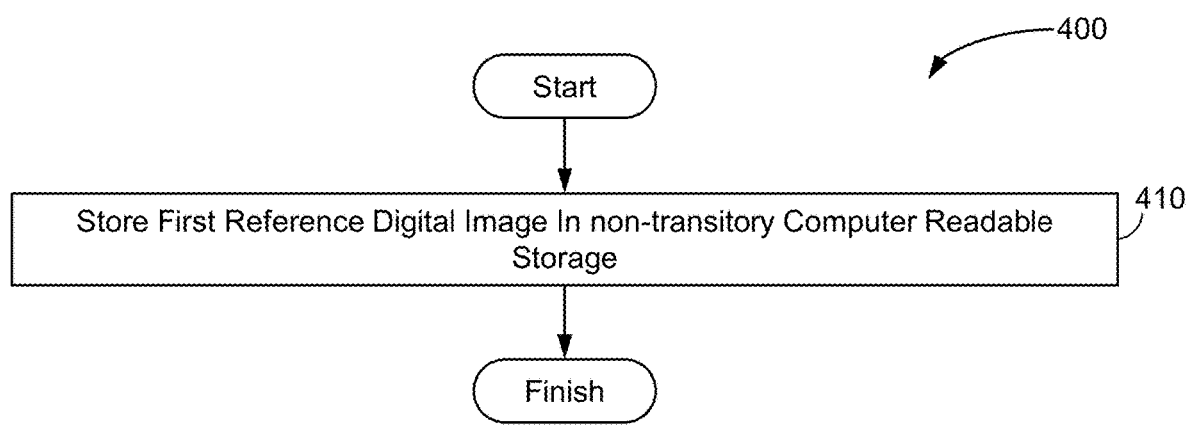

FIG. 4B illustrates method 400, in accordance with one or more implementations. An operation 410 may include further including storing the first reference digital image in a computer readable storage. Operation 410 may be performed by one or more hardware processors configured by machine-readable instructions including a module that is the same as or similar to reference image storing module 316, in accordance with one or more implementations.

System 300 with machine language processing enables real-time confirmation of the surgical site to prevent among other things, wrong site surgery. System 300 leverages smart device camera technology and computer vision science. With image processing and artificial intelligence, the system 300 can automatically map anatomic landmarks/outlines with adjustable image overlay functionalities to accurately and precisely identify the correct site to be treated prior to surgery. System 300 may also integrate across various Electronic Health Records (EHR) and enables secure importing/exporting of images to and from the software application, in according to an implementation. System 300 provides a cost-effective, HIPAA-compliant, and user-friendly method to enhance quality and safety to patients and improvement of computer technology.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A computer implemented method, the method comprising:
   identifying and storing anatomical landmarks and at least one background legion on a first reference digital image of a region of a human body;
   generating a depth map from the first reference digital image of a region of a human body;
   receiving biopsy site identification data on the first reference digital image with the anatomical landmarks and the at least one background legion to form a second reference digital image;
   transforming the second reference digital image into a mesh mask image including the biopsy site identification data;
   overlaying the mesh mask image on a third digital image of the region of the human body; and
   aligning the mesh mask image on the third digital image using said depth map;
   responsive to said overlaying step, comparing whether said biopsy site identification data associated with said mesh mask image and the third digital image has changed.

2. The method of claim 1, further comprising storing the first reference digital image in a non-transitory computer readable storage.

3. The method of claim 1, wherein the third digital image comprising a real-time format.

4. A system, the system comprising:
   one or more hardware processors configured by machine-readable instructions to:
   identify and store anatomical landmarks and at least one background legion on a first reference digital image of a region of a human body;
   generate a depth map from the first reference digital image of a region of a human body;
   receive biopsy site identification data on the first reference digital image with the anatomical landmarks and the at least one background legion to form a second reference digital image;
   transform the second reference digital image into a mesh mask image including the biopsy site identification data;
   overlay the mesh mask image on a third digital image of the region of the human body; and align the mesh mask image on the third digital image using said depth map;

responsive to said overlay step, comparing whether said biopsy site identification data associated with said mesh mask image and the third digital image has changed.

5. The system of claim 4, wherein the one or more hardware processors are further configured by machine-readable instructions to store the first reference digital image in a non-transitory computer readable storage.

6. The system of claim 4, wherein the third digital image comprising a real-time format.

7. A computing platform, the computing platform comprising:

a non-transitory computer-readable storage medium having executable instructions embodied thereon; and one or more hardware processors configured to execute the instructions to:

identify and store anatomical landmarks and at least one background legion on a first reference digital image of a region of a human body;

generate a depth map from the first reference digital image of a region of a human body;

receive biopsy site identification data on the first reference digital image with the anatomical landmarks and the at least one background legion to form a second reference digital image;

transform the second reference digital image into a mesh mask image including the biopsy site identification data;

overlay the mesh mask image on a third digital image of the region of the human body; and align the mesh mask image on the third digital image using said depth map;

responsive to said align step, compare whether said biopsy site identification data associated with said mesh mask image and the third digital image has changed.

8. The computing platform of claim 7, wherein the one or more hardware processors are further configured by the instructions to store the first reference digital image in a non-transitory computer readable storage.

9. The computing platform of claim 7, wherein the third digital image comprising a real-time format.

10. A computer implemented method, the method comprising:

identifying and storing anatomical landmarks and at least one background legion on a first reference digital image of a region of a human body;

generating a depth map from the first reference digital image of a region of a human body;

inserting biopsy site identification data on the first reference digital image with the anatomical landmarks and the at least one background legion to form a second reference digital image;

transforming the second reference digital image into an adjustable transparent mask image including the biopsy site identification data; and overlaying the adjustable transparent mask image on a third digital image of the region of the human body; and aligning the adjustable transparent mask image on the third digital image using said depth map;

responsive to said aligning step, comparing whether said biopsy site identification data associated with said adjustable transparent mask image and the third digital image has changed.

11. The method of claim 10, further comprising storing the first reference digital image in a computer storage.

12. The method of claim 10, wherein the third digital image comprising a real-time format.

\* \* \* \* \*